United States Patent [19]

Bleeker et al.

[11] Patent Number: 4,539,126

[45] Date of Patent: Sep. 3, 1985

[54] BORATED BASIC METAL SALT AND LUBRICATING OIL COMPOSITION

[75] Inventors: Jan J. Bleeker; Martin Booth; Madeline G. F. M. van Grieken; Wilhelmus J. Krijnen; Gerhard d. van Wijngaarden, all of Amsterdam, Netherlands

[73] Assignee: Shell Oil Company, Houston, Tex.

[21] Appl. No.: 671,707

[22] Filed: Nov. 15, 1984

[30] Foreign Application Priority Data

Nov. 15, 1983 [GB] United Kingdom ............... 8330441

[51] Int. Cl.³ ............................................. C10M 1/54
[52] U.S. Cl. ..................................... 252/39; 252/49.6; 252/49.7; 568/6
[58] Field of Search ....................... 252/39, 33.6, 49.7; 568/6

[56] References Cited

U.S. PATENT DOCUMENTS 3,629,109 12/1971 Gergel et al. ......................... 252/33
3,829,381 8/1974 Le Suer ............................. 252/33.4

FOREIGN PATENT DOCUMENTS 271350 8/1964 Australia ................................ 568/6
786167 9/1954 United Kingdom .
1137819 6/1967 United Kingdom .
1146925 6/1967 United Kingdom .

*Primary Examiner*—Jacqueline V. Howard
*Attorney, Agent, or Firm*—Kimbley L. Muller

[57] ABSTRACT

Oil-soluble reaction product of an oil-soluble basic alkaline earth metal salt of an organic acid, in particular of an aromatic carboxylic acid and a boron compound, in particular a boric acid. This product has superior detergent, anti-wear and anti-corrosion properties in engine oils.

4 Claims, No Drawings

BORATED BASIC METAL SALT AND LUBRICATING OIL COMPOSITION

BACKGROUND OF THE INVENTION

This invention relates to a borated basic metal salt, to its preparation and to an oil composition, preferably a lubricating oil composition or a concentrate or a fuel, containing it.

Borated basic calcium salts prepared by contacting a basic calcium petroleum sulfonate with boric acid are known from U.S. Pat. No. 3,829,381, which is incorporated herein by reference. The treatment with boric acid improves the anti-rust properties of these metallic detergents in lubricating oils and fuels.

It has now been found that the treatment with certain boron compounds of a special class of metallic detergents unexpectedly improves the anti-wear properties of oils such as lubricating oils, in particular of engine oils, especially as to wear of cams and tappets. The bearing corrosion properties are improved as well.

SUMMARY OF THE INVENTION

Therefore this invention relates to an oil-soluble reaction product of an oil-soluble basic alkaline earth metal salt of an organic acid, selected from the group of carboxylic acids and alkyl-substituted phenolic compounds, and a boron compound selected from the group of a boric acid, $B_2O_3$ and esters of a boric acid and alcohols, preferably $C_{1-4}$ alkanols.

Suitable basic alkaline earth metal (e.g., calcium or magnesium) salts of organic acids are described in e.g., British patent specification Nos. 1,137,819 and 1,146,925 and a suitable preparation method for these salts is described in e.g., British patent specification No. 786,167, all of which are incorporated herein by reference.

Preferred salts are basic magnesium and calcium salts of naphthenic acids and in particular of alkyl salicylic acids, e.g., $C_{8-30}$-alkyl salicylic acids.

Preferred boron compounds are ortho boric acid ($H_3BO_3$) and metha boric acid ($HBO_2$). Tetra boric acid ($H_2B_4O_7$) can also be used.

PREFERRED EMBODIMENTS OF THE INVENTION

The present products are preferably prepared by after boration, i.e., by reacting the basic metal salt, the basicity of which has preferably been obtained by carbonating with $CO_2$, or a concentrate thereof in e.g., a mineral lubricating oil, with the boron compound, e.g., as a powder or as a slurry in e.g., xylene or as a solution in an alcohol, water or mixture of alcohol and water, e.g., in a solvent, such as a hydrocarbon solvent, e.g., xylene or a mineral lubricating oil at low or high temperatures, e.g., at a temperature between 20° and 200° C., at under-, normal- or over-pressure, preferably at reflux temperature with azeotropic removal of reaction water when a volatile solvent is used, at a mole ratio boron:alkaline earth metal between 0.1 and 10, in a suitable reactor, cooling, if necessary depressurizing, removing any solids, e.g., by filtration or centrifugation, and evaporating the volatile solvent, if present.

The reaction products of this invention including mixtures thereof can be incorporated in oil compositions, in particular lubricating oil compositions or concentrates or fuels, e.g., automotive crankcase oils, in concentrations within the range of 0.001 to 65, in particular 0.1 to 15%w based on the weight of the total compositions.

The lubricating oils to which the additives of the invention can be added include not only mineral lubricating oils, but synthetic oils also. Synthetic hydrocarbon lubricating oils may also be employed, as well as non-hydrocarbon synthetic oils including dibasic acid esters such as di-2-ethyl hexyl sebacate, carbonate esters, phosphate esters, halogenated hydrocarbons, polysilicones, polyglycols, glycol esters such as $C_{13}$ oxo acid diesters of tetraethylene glycol, etc. Mixtures of these oils, in particular of mineral lubricating oils, including hydrogenated oils, and synthetic lubricating oils, can also be used.

When used in gasoline or fuel oil, e.g., diesel fuel, etc., then usually 0.001 to 0.5%w, based on the weight of the total composition of the reaction product will be used. Usually concentrates comprising e.g., 15 to 65%w of said reaction product in a hydrocarbon diluent and 85 to 35%w mineral lubricating oil, are prepared for ease of handling.

In the above compositions other additives may also be present, including dyes, pour point depressants, anti-wear, e.g., tricresyl phosphate, zinc dithiophosphates, antioxidants such as phenyl-alpha-napthyl-amine, bisphenols such as 4,4'-methylene bis(3,6-di-tert-butyl-phenol), viscosity index improvers, such as hydrogenated (co)polymers of conjugated dienes and optionally styrene, ethylene-higher olefin copolymers, polymethylacrylates, polyisobutylene, and the like as well as ashless dispersants, such as reaction products of polyisobutylene, maleic anhydride and amines and/or polyols, or other metal-containing detergents, such as overbased metal salicylates.

Reaction products of amines, formaldehyde and alkyl phenols (Mannich bases) can also be present.

The invention is further illustrated by the following Examples.

EXAMPLE 1

Preparation of borated basic Mg salicylate.

A 5 liter round-bottom flash equipped with a thermocouple, Dean and Stark apparatus and a stirrer was filled with 1000 g of a basic $C_{14-18}$ alkyl Mg salicylate (7.3 eq. Mg/eq. acid (product A) and 1000 g xylene. After heating to about 120° C. 235 g $H_3BO_3$ was added (carefully to avoid excessive foaming). Mole ratio B/Mg 1.29. Then the temperature was gradually increased further to 145° C., while azeotropically removing the reaction water. This took about 1.5 h after which the contents were cooled down to room temperature and filtered. The product was then freed from solvent by stripping in vacuo. (Product B) (1040 g).

Product B contained 7.2 eq. Mg/eq. acid, 6.5%w Mg 3.05%w B, mole ratio B/Mg 1.2 ($H_3BO_3$ conversion 90%).

EXAMPLE 2

Preparation of borated basic Mg salicylate.

5000 kg xylene and 4910 kg of a concentrate of Product A in a mineral lubricating oil (29%w oil) were mixed and heated to 95° C. in a reactor.

1050 kg $H_3BO_3$ were dosed into the reactor in 1 h 15 m in as powder and then the reactor was sealed.

The temperature was increased to 130° and then to 140° C. in 1 h and 2 h 20 min total time, respectively. The pressure was maintained at 1 bar overpressure.

The heating was then discontinued and the reactor depressurized during 1 h.

The reactor was cooled to 60° C. in about 25 min and any solids still present were removed by centrifugation.

The xylene was removed by flashing at 170°-180° C. and nitrogen stripping was used to adjust the flash point. 5000 kg of concentrate of borated basic Mg salicylate (Product C) in the oil were obtained. This concentrate contained (based on concentrate) 7.5 eq. Mg/eq. acids, 6.7%w Mg, 3.4%w B, mole ratio B/Mg 1.1.

TESTS

1. The following formulations were tested, the final formulations being 15W/40 oils.

| Component | I<br>% w | II<br>% w |
|---|---|---|
| Basic Ca salicylate | 2.3 | 2.3 |
| Product A | 1.0 | — |
| Product C | 1.0 | 1.15 |
| Commercial additive package | 5.9 | 5.9 |
| Balance HVI mineral lubricating oil | | |

Formulation I contained a non-borated basic Mg salicylate. Formulation II was according to the invention. CRC L38 performance (ASTM STP 509A, part IV).

The Cu/Pb bearing weight loss is represented in Table I.

TABLE I

| Formulation | I | II | API/SF/CD limit* |
|---|---|---|---|
| Bearing weight loss, mg | 36.8 | 14.7 | 40 max. |

*(combining diesel with gasoline engine performance) (API = American Petroleum Institute).

This Table shows the very low bearing weight loss of formulation II according to the invention.

2. The following formulations were tested, the final formulations being 15W/40 oils.

| Component | III<br>% w | IV<br>% w |
|---|---|---|
| Basic Ca salicylate | 2.3 | 2.3 |
| Product A | 0.95 | — |
| Product C | — | 1.11 |
| Commercial additive package | 7.62 | 7.62 |
| Balance HVI mineral lubricating oil | | |

Formulation III contained a non-borated Mg salicylate. Formulation IV was according to the invention.

MS Sequence III D performance

This method describes an engine test procedure for evaluating inter alia engine wear of engine oils.

The results are represented in Table II.

TABLE II

| Formulation | III | | | | IV | | API/SF/CD limits |
|---|---|---|---|---|---|---|---|
| Maximum cam wear, mm | 0.375 | 0.412 | 0.662 | 4.37 | 0.122 | 0.152 | 0.20 max |
| Average cam wear, mm | 0.16 | 0.187 | 0.38 | 0.435 | 0.065 | 0.065 | 0.10 max |

This Table again shows the very low wear of formulation III according to the invention. This was obtained without a substantial change in the cleanliness properties.

EXAMPLE 3

Preparation of borated basic magnesium alkyl salicylate with meta boric acid.

A 3 liter round-bottom flask equipped with a thermocouple, Dean and Stark apparatus and a stirrer is loaded with 113 g ortho boric acid and 500 g xylene. The boric acid is converted into meta boric acid by heating and removing the reaction water by azeotropic distillation in about 1.5 h. After cooling to 70° C. 500 g of the same concentrate of the basic magnesium alkylsalicylate is added as used in Example 2.

Subsequently the reactor contents are heated to 140° C. and then kept at this temperature for an additional 3 h. After cooling to room temperature the reaction mixture is centrifuged and the solvent is removed in vacuo. The product contains 3.4%w B and 6.05%w Mg.

EXAMPLE 4

Preparation of borated basic calcium alkylsalicylate.

A 3 liter round-bottom flask equipped with a thermocouple, Dean and Stark apparatus and a stirrer is loaded with 500 g of a concentrate of a basic $C_{14}$-$C_{18}$ alkylsalicylate in lubricating oil (product D) with the following analysis:

TBN = 286 mg KOH/g
metal ratio = 7.9 eq. Ca/eq. acid

After addition of 500 g xylene the resulting solution is heated to 95° C. while stirring. Then 50 g of orthoboric acid is added. The B/Ca molar ratio in the reaction mixture is then 0.63. Thereafter the temperature is gradually increased to 145° C., while the reaction water is removed by azeotropic distillation. This takes bout 1.5 h. Subsequently the reactor contents are filtered on metal gauze and after cooling the solution is centrifuged to remove any residual solids present. Finally the xylene is removed in vacuo. The resulting concentrate is analyzed to contain 9.27%w Ca, equivalent with a TBN of 260 mg KOH/g and 1.8%w B.

EXAMPLES 5-8

Using the procedure of example 4 but with higher amounts of orthoboric acid examples 5-8 were prepared, also shown in Table III.

TABLE III

| | | Product Analysis | | |
|---|---|---|---|---|
| Example | B/Ca intake molar ratio | metal ratio | Ca content % w | B content % w |
| product D | 0 | 7.9 | 10.2 | 0 |
| 4 | 0.63 | 8.0 | 9.27 | 1.8 |
| 5 | 1.27 | 8.0 | 8.74 | 2.9 |
| 6 | 1.90 | 8.0 | 8.29 | 4.0 |
| 7 | 2.53 | 8.0 | 7.88 | 4.8 |
| 8 | 4.02 | 7.8 | 7.05 | 6.4 |

EXAMPLE 9

Preparation of a borated basic calcium naphthenate.

Exactly according to example 4, but using a 0.5 liter round-bottom flask, a borated basic calcium naphthenate is made using 100 g of a concentrate of a basic calcium naphthenate in lubricating oil with the following analysis:

TBN=238 mg KOH/g metal ratio=8.4 eq. Ca/eq. acid 100 g xylene and 33 g orthoboric acid. The resulting concentrate contains 6.33%w Ca and 3.1%w B. The metal molar ratio was 6.5 which indicates that the product lost some calcium during the preparation.

What is claimed is:

1. An oil soluble reaction product of the reaction of an oil soluble basic magnesium or calcium salt of an organic acid consisting essentially of a magnesium or calcium $C_{8-30}$ alkyl salicylate and a boron compound selected from the group consisting of ortho boric acid, meta boric acid and tetra boric acid, wherein said reaction is effected at a temperature of from about 20° to about 200° C. and at a mole ratio of said boron to said magnesium or calcium $C_{8-30}$ alkyl salicylate of between 0.1 to 10.

2. A process for preparation of the boron-containing soluble basic magnesium or calcium salicylate of claim 1 which comprises reacting, at reaction conditions, including a temperatue of from about 20° to about 200° C., a magnesium or calcium $C_{8-30}$ alkyl salicylate with a boron compound selected from the group consisting of ortho boric acid, meta boric acid and tetra boric acid in a mole ratio of boron to said salicylate of between 0.1 to 10.0.

3. The product of claim 1 further defined in association with a lubricating oil in an amount of from 0.001-65 weight % based on the weight of the total composition.

4. The product of claim 1 further defined in association with a fuel oil in an amount of from 0.001 to 0.5 weight percent based on the weight of the total composition.

* * * * *